(12) United States Patent
Lefort et al.

(10) Patent No.: US 10,947,170 B2
(45) Date of Patent: *Mar. 16, 2021

(54) PROCESS FOR THE PREPARATION OF DEUTERATED ETHANOL FROM $D_2O$

(71) Applicant: Deuteria Beverages, LLC, Reno, NV (US)

(72) Inventors: Laurent Lefort, Maastricht (NL); Mike Schmitkamp, Herzogenrath (DE)

(73) Assignee: DEUTERIA BEVERAGES, LLC., Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/693,308

(22) Filed: Nov. 24, 2019

(65) Prior Publication Data
US 2020/0165175 A1    May 28, 2020

Related U.S. Application Data

(63) Continuation of application No. 15/964,017, filed on Apr. 26, 2018, now Pat. No. 10,494,316.

(60) Provisional application No. 62/491,185, filed on Apr. 27, 2017.

(51) Int. Cl.
| | | |
|---|---|---|
| *C07B 59/00* | (2006.01) | |
| *B01J 31/18* | (2006.01) | |
| *C07C 29/80* | (2006.01) | |
| *C07C 29/90* | (2006.01) | |
| *B01J 31/24* | (2006.01) | |
| *B01J 31/22* | (2006.01) | |
| *C07C 29/00* | (2006.01) | |
| *B01J 31/20* | (2006.01) | |
| *A61K 31/045* | (2006.01) | |
| *C12C 12/00* | (2006.01) | |
| *A61K 9/00* | (2006.01) | |
| *C12G 1/00* | (2019.01) | |
| *C12G 3/00* | (2019.01) | |

(52) U.S. Cl.
CPC ......... *C07B 59/001* (2013.01); *B01J 31/1805* (2013.01); *B01J 31/189* (2013.01); *B01J 31/20* (2013.01); *B01J 31/2213* (2013.01); *B01J 31/2295* (2013.01); *B01J 31/2409* (2013.01); *B01J 31/2414* (2013.01); *C07C 29/00* (2013.01); *C07C 29/80* (2013.01); *C07C 29/90* (2013.01); *A61K 9/0095* (2013.01); *A61K 31/045* (2013.01); *B01J 31/1815* (2013.01); *B01J 31/2239* (2013.01); *B01J 2231/40* (2013.01); *B01J 2531/821* (2013.01); *B01J 2531/827* (2013.01); *C07B 2200/05* (2013.01); *C07B 2200/07* (2013.01); *C12C 12/00* (2013.01); *C12G 1/00* (2013.01); *C12G 3/00* (2013.01)

(58) Field of Classification Search
CPC ... C07B 59/00; C07B 59/001; C07B 2200/05; C07C 29/00; B01J 31/189; B01J 2531/821
See application file for complete search history.

(56) References Cited

U.S. PATENT DOCUMENTS

| | | |
|---|---|---|
| 8,003,838 B2 | 8/2011 | Dupau et al. |
| 10,343,955 B2 | 7/2019 | Lefort et al. |
| 2008/0145303 A1 | 6/2008 | Hirota et al. |
| 2008/0234488 A1 | 9/2008 | Ito et al. |
| 2011/0237814 A1 | 9/2011 | Kuriyama et al. |
| 2013/0303774 A1 | 11/2013 | Ishii et al. |
| 2014/0081019 A1 | 3/2014 | Atzrodt et al. |
| 2016/0039853 A1 | 2/2016 | Dupau et al. |
| 2016/0130194 A1 | 5/2016 | Howard, Jr. et al. |

OTHER PUBLICATIONS

Maegawa, T., et al., A Convenient and Selective Method for the Regioselective Deuteration of Alcohols, Adv. Synth Catal. 2008, 350, 2215-18.
Zhang, Lei et al., Efficient deuterium labelling of alcohols in deuterated water catalyzed by ruthenium pincer complexes, Catalysis Communications 2016, 84, 67-70.
Chatterjee Basujit et al., The ruthenium-catalyzed selective synthesis of mono-deuterated terminal alkynes, Chem. Commun. 2016, 52, 4509-12.
Chatterjee Basujit et al., Ruthenium Catalyzed Selective a- and a,b-Deuteration of Alcohols Using D2O, Or. Lett. 2015, 17, 4794-97.
PCT/US18/029658 Written Opinion dated Jul. 24, 2018 (corresponding PCT application).
PCT/US18/029658 International Search Report dated Jul. 24, 2018 (corresponding PCT application).
Kashkin et al., Simple and Effective Catalytic Reaction for Selective Deuteration of Alcohols, Catalysis 2013, 3, 448-52.

*Primary Examiner* — Yate' K Cutliff
(74) *Attorney, Agent, or Firm* — Vance Intellectual Property PC

(57) ABSTRACT

The invention relates to a process for the preparation of a deuterated ethanol from ethanol, $D_2O$, a ruthenium catalyst, and a co-solvent.

24 Claims, No Drawings

PROCESS FOR THE PREPARATION OF DEUTERATED ETHANOL FROM D₂O

FIELD OF THE INVENTION

The present invention relates to a process for the preparation of a deuterated ethanol from D$_2$O.

BACKGROUND OF THE INVENTION

Deuterium (D or $^2$H) is a stable, non-radioactive isotope of hydrogen. Deuterium-enriched organic compounds such as a deuterated ethanol are known. U.S. Pat. No. 8,658,236 describes an alcoholic beverage of water and ethanol, wherein at least 5 mole percent of the ethanol is a deuterated ethanol. This alcoholic beverage is believed to diminish the negative side effects associated with the consumption of ethanol.

The production of a deuterated-ethanol containing alcoholic beverage requires the preparation of a deuterated ethanol in an efficient, safe, and cost-effective manner. A known process for the preparation of a deuterated alcohol (e.g., deuterated ethanol) involves an H/D exchange reaction between a non-deuterated alcohol and D$_2$O. Depending on the process, the resulting deuterated alcohol may comprise deuterium in different positions. Examples of such processes can be found in Chemistry Letters 34, No. 2 (2005), p. 192-193 "Ruthenium catalyzed deuterium labelling of α-carbon in primary alcohol and primary/secondary amine in D$_2$O"; Adv. Synth. Catal. 2008, 350, p. 2215-2218 "A method for the regioselective deuteration of alcohols"; Org. Lett. 2015, 17, p. 4794-4797 "Ruthenium Catalyzed Selective α- and α,β-Deuteration of Alcohols Using D$_2$O" and Catalysis Communications 84 (2016) p. 67-70 "Efficient deuterium labelling of alcohols in deuterated water catalyzed by ruthenium pincer complexes".

Other routes to produce a deuterated alcohol involve several consecutive reactions requiring expensive and/or hazardous material. For each of these transformations, purification and isolation of the intermediates are necessary.

In view of the above, it is desirable to be able to synthesize deuterated ethanol in an efficient, safe and cost-effective manner. It is further desirable to synthesize deuterated ethanol with deuteration substantially only at a desired position(s).

SUMMARY OF THE INVENTION

In an aspect, the present invention provides a process for the preparation of a deuterated ethanol from ethanol, D$_2$O, a ruthenium catalyst, and a co-solvent.

These and other aspects, which will become apparent during the following detailed description, have been achieved by the inventors' discovery of a new process of making deuterated ethanol.

DETAILED DESCRIPTION OF THE INVENTION

It has now surprisingly been found that the combination of D$_2$O, a ruthenium catalyst, and co-solvent allows for the effective and selective deuteration of ethanol.

Catalysis Communications 2016, 84, 67-70 (CC), mentions the deuteration of alcohol catalyzed by Ru-MACHO®-BH and Ru-MACHO®, but fails to mention the use of a co-solvent. Ru-MACHO®-BH was used only for the deuteration of 1-butanol and not ethanol. It has now been found that no deuteration of ethanol occurs when 1-butanol is replaced by ethanol in the system described in CC where the catalyst is Ru-MACHO®-BH.

CC also mentions the deuteration of ethanol catalyzed by Ru-MACHO® using 20 mol % of NaOH. It has now been found that deuteration of ethanol is not possible when NaOH is replaced by another base in the system described in CC where the catalyst is Ru-MACHO®. However, it has surprisingly been discovered that the addition of a co-solvent to dissolve the catalyst results in an efficient deuteration of ethanol, in particular without the presence NaOH.

Thus, in an aspect, the present invention provides a novel process for the preparation of a deuterated ethanol of formula (I):

$$CR^1R^2R^3CR^4R^5OD \quad (I)$$

comprising: reacting ethanol and D$_2$O in the presence of a ruthenium catalyst of formula (II) and a co-solvent:

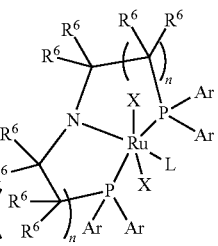

(II)

whererin:
R$^1$-R$^5$ are independently H or D, provided that the abundance of D in R$^4$ and R$^5$ is at least 70%;
each R$^6$ is independently selected from: H, a C$_{1-10}$ alkyl group, a substituted C$_{1-10}$ alkyl group, a C$_{6-18}$ aromatic ring group, and a substituted C$_{6-18}$ aromatic ring group;
each Ar is independently selected from a C$_{6-18}$ aromatic ring group and a substituted C$_{6-18}$ aromatic ring group;
each n is independently 1 or 2;
L is a ligand;
X is a counterion; and,
the catalyst is soluble in the mixture of ethanol, D$_2$O, and the co-colvent.

In another aspect, the process is performed in the absence of a base.

In another aspect, the process is performed in the absence of NaOH.

The abundance of D in R$^4$ and R$^5$ (the CH$_2$ position) and in R$^1$, R$^2$, and R$^3$ (the CH$_3$ position) can be measured by $^1$H NMR. The 70% abundance of D in R$^4$ and R$^5$ means that 70% of all R$^4$ and R$^5$ present are D (as opposed to the natural abundance of 0.01%).

In another aspect, the abundance of D in R$^4$ and R$^5$ is at least 80%. Additional examples of the abundance of D in R$^4$ and R$^5$ include at least 90, 91, 92, 93, 94, 95, 96, 97, 98, 99, and 99.5%.

In another aspect, the incorporation of D occurs preferentially in R$^4$ and R$^5$ over R$^1$-R$^3$. In another aspect, the abundance of D in R$^1$-R$^3$ is at most 50%. Additional examples of the abundance of D in R$^1$-R$^3$ include at most 45, 40, 35, 30, 25, 20, 15, 10, 5, and 1%.

In another aspect, the abundance of D in R$^4$ and R$^5$ is at least 90% and the abundance of D in R$^1$-R$^3$ is at most 5%. Additional examples include (a) at least 95% and at most 1%, and (b) at least 99% and at most 1%.

The conversion of ethanol to deuterated ethanol in the present process can be determined by ¹H NMR. The conversion is the molar ratio of deuterated ethanol formed divided by the initial amount of starting ethanol (un-enriched ethanol). In an aspect, the conversion percentage (molar ratio×100) is at least 90%. Additional examples of the conversion percentage include at least 95%, at least 98%, and at least 99%. The co-solvent forms a mixture together with ethanol and $D_2O$, which solubilizes the catalyst. Examples of co-solvents include tetrahydrofuran (THF), 2-methyltetrahydrofuran, methyl tert-butyl ether (MTBE), diisopropyl ether, 1,2-dimethoxyethane, toluene (tol), benzene, xylenes, 1,4-dioxane, diglyme (diethylene glycol diethyl ether), cyclopentyl methyl ether (CPME), ethyl acetate, 1,2-dichloroethane, dimethylacetamide, dimethylformamide, and dimethyl sulfoxide.

The co-solvent may also be deuterated, wherein one or more H atoms of the co-solvent are replaced by D. Examples of deuterated co-solvents include $d_8$-tetrahydrofuran, $d_8$-toluene, and $d_8$-1,4-dioxane.

The reaction mixture may be monophasic or biphasic. For example, in the case where the co-solvent is toluene or cyclopentyl methyl ether, the mixture is biphasic.

For increasing the loading of the reactor and therefore the productivity, the amount of the co-solvent is typically not too high. Thus, in another aspect, the volume ratio of $D_2O$ to the co-solvent in the reacting step is higher than 0.5. Additional examples of the volume ratio include from 1-30. Further examples of the volume ratio include from, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, to 30. The upper limit for the volume ratio is typically about 30.

In another aspect, the molar ratio of $D_2O$ to ethanol in the reacting step is at least 3. Additional examples of the molar ratio include 3-10, 3-75, and 3-100. Other examples of the molar ratio include at least 3, 4, 5, 6, 7, 8, 9, 10, 11, 12, 13, 14, 15, 16, 17, 18, 19, 20, 21, 22, 23, 24, 25, 26, 27, 28, 29, to 30. This leads to a higher D incorporation at the desired position. The upper limit of the molar ratio is typically or 75 or 100.

The ruthenium catalysts of formula (II) are known (see U.S. Pat. No. 8,003,838, US2013/0303774, and US2016/0039853, which are incorporated herein by reference).

Ligand "L" is any ligand suitable for the deuterium enrichment of ethanol in accordance with the presently claimed invention. In another aspect, the ligand is selected from: a monodentate ligand. Examples of monodentate ligands include phosphine (e.g., triphenylphosphine), carbon monoxide, an olefin, water, acetonitrile, dimethylsulfoxide.

In another aspect, ligand L is carbon monoxide (CO).

In another aspect, counterion X is selected from: pentamethylcyclopentadienyl, chloride, bromide, iodide, hydride, triflate and $BH_4$.

In another aspect, one of the counterions X is hydride.

In another aspect, in formula (II) two vicinal $R^6$ (except hydrogen atoms) may form a cyclic structure by covalent bond of carbon atoms through or without a nitrogen atom, an oxygen atom, or a sulfur atom.

In another aspect, in formula (II), each Ar is phenyl.

In another aspect, n is 1 (each P is bound to the N in the Ru complex via a 2 carbon linker).

In another aspect, n is 2 (each P is bound to the N in the Ru complex via a 3 carbon linker).

In another aspect, n=1 and all $R^6$=hydrogen.

In another aspect, L is carbon monoxide and one of X is hydride.

In another aspect, the catalyst is a Ru complex of formula (III) (which is commercially available as Ru-MACHO®) ({Bis[2-(diphenylphosphino)ethyl]amine}carboynlchlorohydridoruthenium(II)):

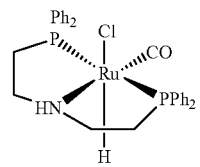

(III)

wherein Ph=phenyl.

In another aspect, the catalyst is the compound of formula (III) and the reaction is performed in the presence of an alkali metal borohydride.

Examples of alkali metal borohydrides include $LiBH_4$, $NaBH_4$, and $KBH_4$.

In another aspect, the catalyst is the compound of formula (III) and the reaction is performed in the presence of $NaBH_4$.

In another aspect, the catalyst is the compound of formula (III) and the reaction is performed in the presence of an alkali metal borohydride and in the absence of NaOH.

In another aspect, the catalyst is the compound of formula (III) and the reaction is performed in the presence of $NaBH_4$ and in the absence of NaOH.

The combination of a suitable co-solvent and an alkali metal borohydride using the compound (III) was found to result high selectivity for the D incorporation in $R^4$-$R^5$ over $R^1$-$R^3$.

In another aspect, the catalyst is a Ru complex of formula (IV) (which is commercially available as Ru-MACHO®-BH) (Carbonylhydrido(tetrahydroborato) [bis(2-diphenylphosphinoethyl)amino]ruthenium(II))):

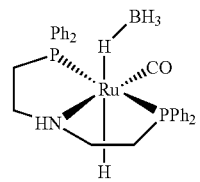

(IV)

wherein Ph=phenyl.

In another aspect, the catalyst is the compound of formula (IV) and the reaction is performed in the absence of a base.

The combination of the catalyst of formula IV and a suitable co-solvent was found to result high selectivity for the D incorporation in $R^4$-$R^5$ over $R^1$-$R^3$.

The deuterated ethanol (I) may be obtained by reacting the total amount of $D_2O$ with ethanol in one step (as described above) or reacting $D_2O$ in multiple steps with a distillation step between the mixing steps (as described as follows). Thus, in another aspect, the reacting step, comprises:

a. reacting a first portion of $D_2O$ with ethanol,
b. collecting a distillate from the reacted mixture, and
c. adding a second portion of $D_2O$ to the distillate to further react unreacted ethanol with $D_2O$.

In another aspect, after step c), the process, further comprises: repeating steps b) and c) one or more times until the desired level of D incorporation is achieved.

Accordingly, in another aspect, the reacting step, comprises:
a. reacting a first portion of $D_2O$ with ethanol;
b. collecting a distillate from the reacted mixture;
c. adding a second portion of $D_2O$ to the distillate to further react with unreacted ethanol;
d. collecting a distillate from the reacted mixture; and,
e. adding a third portion of $D_2O$ to the distillate to further react with unreacted ethanol.

In another aspect, the reacting step, comprises:
a. reacting a first portion of $D_2O$ with ethanol;
b. collecting a distillate from the reacted mixture;
c. adding a second portion of $D_2O$ to the distillate to further react with unreacted ethanol;
d. collecting a distillate from the reacted mixture;
e. adding a third portion of $D_2O$ to the distillate to further react with unreacted ethanol;
f. collecting a distillate from the reacted mixture; and
g. adding a fourth portion of $D_2O$ to the distillate to further react with unreacted ethanol.

When multiple steps are used, the amount of $D_2O$ required for achieving the desired D incorporation in ethanol is advantageously reduced compared to the case where the total amount of $D_2O$ is mixed with ethanol in one step. In step a), a first portion of $D_2O$ is reacted with ethanol to obtain a partly reacted mixture with a certain degree of D incorporation in ethanol. This partly reacted mixture also comprises $H_2O$ formed as a by-product of the D incorporation in ethanol, which inhibits the further D incorporation in ethanol. In step b), this partly reacted mixture is subjected to distillation to collect a distillate that mainly comprises deuterated and non-deuterated ethanol. The distillate comprises only a very small amount of $H_2O$. A second portion of $D_2O$ is added to the distillate, which allows further D incorporation.

In another aspect, the molar ratio of $D_2O$ to ethanol mixed in the reacting step in each of the reaction sub-steps (a/c, a/c/e, a/c/e/g, etc.) is selected from 1, 2, 3, 4, and 5.

In another aspect, the reaction temperature is at most 200° C. Examples of the reaction temperature include from 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, to 180° C. Additional examples include from 50-160° C. Further examples include from 50, 55, 60, 65, 70, 75, 80, 85, 90, 95, 100, 105, 110, 115, 120, 125, 130, 135, 140, 145, 150, 155, to 160° C.

In another aspect, the reaction is performed at a period of 0.5, 1, 5, 10, 15, 20, 25, 30, 35, 40, 45, 50, 55, 60, 65, 70, 75, 80, 85, 90, 95 to 100 hours. Examples of the time the reaction is performed include from 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70 to 72 hours.

In another aspect, compound (I) can be separated from the reaction product by any ordinary post treatment operation for organic synthesis. Further, the crude product can be purified to a high purity, as needed, by standard methods including, activated carbon treatment, fractional distillation, recrystallization, and column chromatography. It can be convenient to directly subject the completed reaction solution to a distillation recovery operation.

In the case where the reaction is performed in the presence of a base, the target compound of relatively high acidity tends to form a salt or complex with the base used and remain in the distillation residue during distillation recovery operation. In such a case, the target compound can be obtained with high yield by neutralizing the reaction completed solution with an organic acid (e.g., formic acid, acetic acid, citric acid, oxalic acid, benzoic acid, methanesulfonic acid or paratoluenesulfonic acid) or an inorganic acid (e.g., HCl, HBr, $HNO_3$, $H_2SO_4$) in advance, and then, subjecting the neutralized reaction completed solution to a distillation recovery operation (including recovery by washing the distillation residue with an organic solvent such as diisopropyl ether).

It is noted that the invention relates to all possible combinations of features described herein. It will therefore be appreciated that all combinations of features relating to the composition according to the invention; all combinations of features relating to the process according to the invention and all combinations of features relating to the composition according to the invention and features relating to the process according to the invention are described herein.

It should be understood that a description on a product/composition comprising certain components also discloses a product/composition consisting of these components. The product/composition consisting of these components may be advantageous in that it offers a simpler, more economical process for the preparation of the product/composition. Similarly, it should be understood that a description on a process comprising certain steps also discloses a process consisting of these steps. The process consisting of these steps may be advantageous in that it offers a simpler, more economical process.

DEFINITIONS

The examples provided in the definitions present in this application are non-inclusive unless otherwise stated. They include but are not limited to the recited examples.

When values are mentioned for a lower limit and an upper limit for a parameter, ranges made by the combinations of the values of the lower limit and the values of the upper limit are also understood to be disclosed.

"Alkyl" includes the specified number of carbon atoms in a linear, branched, and cyclic (when the alkyl group has 3 or more carbons) configuration. Alkyl includes a lower alkyl groups ($C_1$, $C_2$, $C_3$, $C_4$, $C_5$, and $C_6$ or 1-6 carbon atoms). Alkyl also includes higher alkyl groups ($>C_6$ or 7 or more carbon atoms).

When an "ene" terminates a group it indicates the group is attached to two other groups. For example, methylene refers to a —$CH_2$-moiety.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ alkynyl includes $C_2$, $C_3$, $C_4$, $C_5$, and $C_6$ alkynyl groups.

"Substituted alkyl" is an alkyl group where one or more of the hydrogen atoms have been replaced with another chemical group (a substituent). Substituents include: halo, OH, OR (where R is a lower alkyl group), $CF_3$, $OCF_3$, $NH_2$, NHR (where R is a lower alkyl group), $NR^xR^y$ (where $R^x$ and $R^y$ are independently lower alkyl groups), $CO_2H$, $CO_2R$ (where R is a lower alkyl group), $C(O)NH_2$, $C(O)NHR$ (where R is a lower alkyl group), $C(O)NR^xR^y$ (where $R^x$ and $R^y$ are independently lower alkyl groups), CN, $C_{2-6}$ alkenyl, $C_{2-6}$ alkynyl, $C_{6-12}$ aromatic ring group, substituted $C_{6-12}$ aromatic ring group, 5-12 membered aromatic heterocyclic group, and substituted 5-12 membered aromatic heterocyclic group.

Examples of the aromatic ring group are aromatic hydrocarbon groups as typified by phenyl, naphthyl and anthryl.

Examples of the aromatic heterocyclic group are aromatic hydrocarbon groups containing hetero atoms e.g. as nitrogen, oxygen or sulfur as typified by pyrrolyl (including nitrogen-protected form), pyridyl, furyl, thienyl, indolyl (including nitrogen-protected form), quinolyl, benzofuryl and benzothienyl.

"Substituted aromatic ring group" or "substituted aromatic heterocyclic ring group" refers to an aromatic/aromatic heterocyclic ring group where at least one of the hydrogen atoms has been replaced with another chemical group. Examples of such other chemical groups include: halo, OH, $OCH_3$, $CF_3$, $OCF_3$, $NH_2$, NHR (where R is a lower alkyl group), $NR^xR^y$ (where $R^x$ and $R^y$ are independently lower alkyl groups), $CO_2H$, $CO_2R$ (where R is a lower alkyl group), $C(O)NH_2$, C(O)NHR (where R is a lower alkyl group), $C(O)NR^xR^y$ (where $R^x$ and $R^y$ are independently lower alkyl groups), CN, lower alkyl, aryl, and heteroaryl.

"Halo" refers to Cl, F, Br, or I.

Other features of the invention will become apparent in the course of the following descriptions of exemplary embodiments that are given for illustration of the invention and are not intended to be limiting thereof.

EXAMPLES

The structures of catalyst (II) tested are as follows:

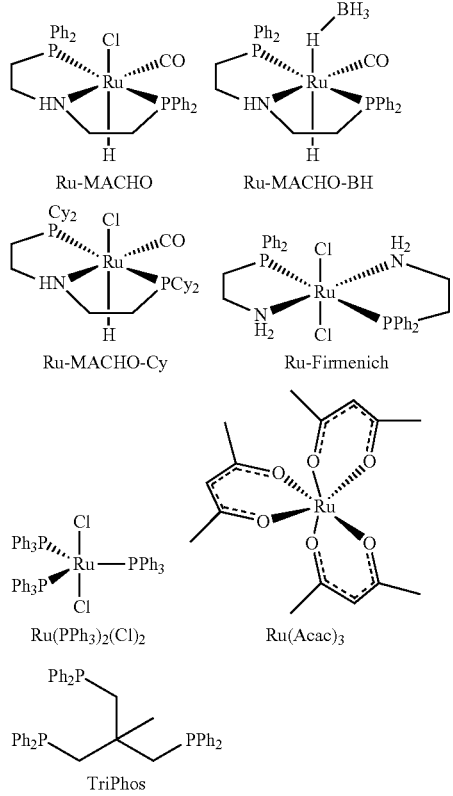

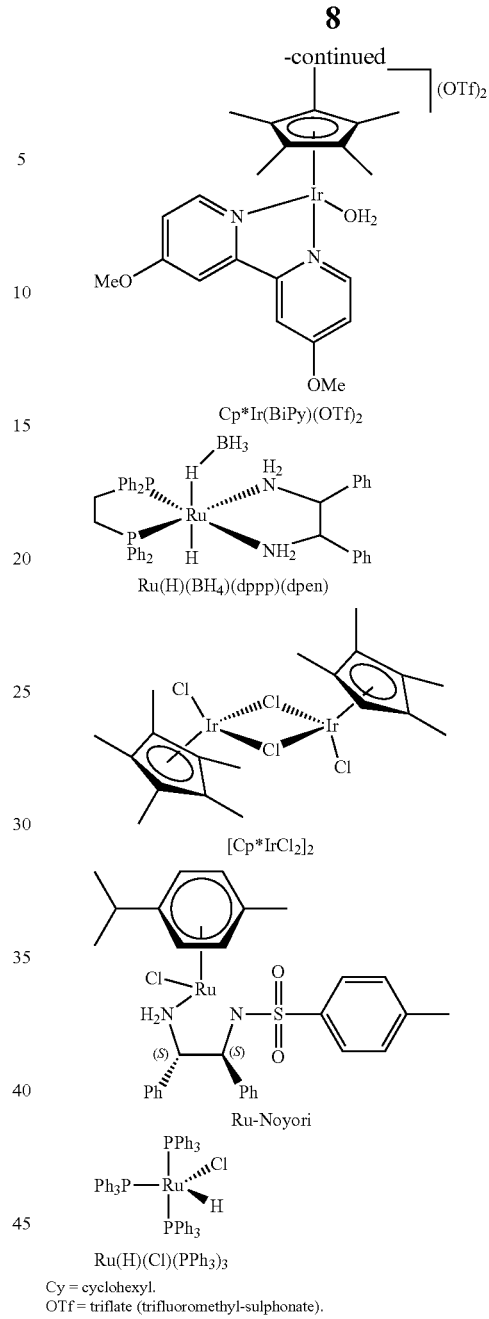

Cy = cyclohexyl.
OTf = triflate (trifluoromethyl-sulphonate).

Experiments were performed by placing the catalyst (and the base when required) inside a 5 mL vial under $N_2$ atmosphere. A mixture of ethanol and $D_2O$ was added followed by the co-solvent when used. The vial was capped and the temperature was increased to the desired reaction temperature while stirring at 500 rpm with a magnetic stirred. After 16 h, the reaction mixture was cooled. After purging with $N_2$, the autoclave was opened and the reaction mixture was analyzed by $^1H$ NMR to determine the D incorporation.

The abundance of D in the $CH_2$ position was determined by the amount of the residual H in the $CH_2$ position. The "residual H at the $CH_2$ position" was determined by the normalized ratio of area of the $CH_2$ signal in the ethanol divided by the area of the $CH_3$ signal in the ethanol. The complement to 100 of this quantity equals to the abundance of D in the $CH_2$ position.

Experiment Set 1

Ru-MACHO®-BH was tested without (Exp 1) and with various co-solvents (Exp 2-10). No base was used. The results are shown in Table 1.

TABLE 1

| Exp | Cat amount (mmol) | Reaction mixture | Ratio 1 (mmol) | Rxn vol (mL) | Ratio 2 | T (°C.) | time (h) | D inc. at $CH_2$ |
|---|---|---|---|---|---|---|---|---|
| 1 | 0.0053 | — | 2.21:15 | 0.5 | 400 | 110 | 16 | 0 |
| 2 | 0.0206 | $d_8$-THF | 5.45:34 | 2 | 250 | 80 | 16 | 82 |
| 3 | 0.0089 | $d_8$-Tol | 4.1:71 | 2.2 | 462 | 80 | 21 | 92 |
| 4 | 0.0155 | CPME | 5.45:34 | 2 | 350 | 80 | 16 | 84 |
| 5 | 0.0162 | Dioxane | 5.45:34 | 2 | 350 | 80 | 16 | >98 |
| 6 | 0.0165 | Diglyme | 5.45:34 | 2 | 350 | 80 | 16 | >98 |
| 7 | 0.0082 | $d_2$-DCM | 4.1:71 | 2.2 | 501 | 80 | 21 | 0 |
| 8 | 0.0082 | $d_3$-$CH_3CN$ | 4.1:71 | 2.2 | 501 | 80 | 21 | 0 |
| 9 | 0.0087 | $d_6$-acetone | 4.1:71 | 2.2 | 471 | 80 | 21 | 0 |
| 10 | 0.0157 | tBuOH | 5.45:34 | 2 | 350 | 80 | 16 | <5 |
| 11 | 0.0148 | NMP | 5.45:34 | 2 | 350 | 80 | 16 | <5 |

Reaction mixture: all reaction mixtures contained EtOH:$D_2O$ and the shown co-solvent. In all cases, the volume of the co-solvent was 1 mL.
Ratio 1 = ratio of EtOH:$D_2O$.
Ratio 2 = mmolar ratio of EtOH:catalyst.
DCM = dichloromethane.
NMP = N-Methyl-2-pyrrolidone.

Experiment 1:

When no co-solvent was used, no D incorporation occurred at the desired $CH_2$ position.

Experiments 2-6:

When a co-solvent of THF (tetrahydrofurane), toluene, CPME (cyclopentyl methyl ether), dioxane or diglyme was used, the catalyst dissolved in the mixture of ethanol, $D_2O$ and the co-solvent and D incorporation occurred at the desired $CH_2$ position.

Experiments 7-11:

When a co-solvent of DCM (dichloromethane), $CH_3CN$, acetone, tBuOH, or NMP (N-Methyl-2-pyrrolidone) was used, little or no D-incorporation occurred at the desired $CH_2$ position.

These results were not dependent on whether the co-solvent was deuterated or not.

Experiment Set 2

Ru-MACHO® was tested without (Exp 12) and with various co-solvents (Exp 13-19).

TABLE 2

| Exp | Catalyst additive | Cat amt (mmol) | Rxn mix | Ratio 1 (mmol) | Rxn vol (mL) | Ratio 2 | T (° C.) | time (h) | D inc. at $CH_2$ |
|---|---|---|---|---|---|---|---|---|---|
| 12 | — | 0.0071 | | 2.21:15 | 0.5 | 300 | 110 | 16 | 0 |
| 13 | $HCO_2Na$ (55 eq/Ru) | 0.0069 | | 4.42:30 | 1 | 650 | 80 | 16 | 0 |
| 14 | $NaHCO_3$ (50 eq/Ru) | 0.0102 | | 4.42:30 | 1 | 450 | 80 | 16 | 0 |
| 15 | $NaBH_4$ (14 eq/Ru) | 0.0160 | | 5.45:34 | 1 | 350 | 80 | 16 | 0 |
| 16 | — | 0.0064 | Tol (0.5 mL) | 2.21:15 | 1 | 350 | 110 | 16 | 0 |
| 17 | $NaBH_4$ (9 eq/Ru) | 0.0058 | Tol (0.5 mL) | 2.21:15 | 1 | 400 | 110 | 16 | 85 |
| 18 | $NaBH_4$ (5 eq/Ru) | 0.0160 | $d_8$-Tol (1 mL) | 5.45:34 | 2 | 350 | 80 | 16 | 80 |
| 19 | $NaBH_4$ (7 eq/Ru) | 0.0160 | Dioxane (1 mL) | 5.45:34 | 2 | 350 | 80 | 16 | 75 |

Rxn Mix (Reaction mixture): all reaction mixtures contained EtOH:$D_2O$ and the shown co-solvent.
Ratio 1 = ratio of EtOH:$D_2O$.
Ratio 2 = mmolar ratio of EtOH:catalyst.

Experiments 12-15:

When no co-solvent was used, no D incorporation occurred at the desired $CH_2$ position independent of the type of the base or the presence of $NaBH_4$.

Experiment 16:

When no $NaBH_4$ was used, no D incorporation occurred at the desired $CH_2$ position independent on the type of co-solvent.

Experiment 17-19:

The combination of a co-solvent and $NaBH_4$ resulted in D incorporation at the desired $CH_2$ position.

Experiment Set 3

Various types of catalysts were tested in the absence of a co-solvent or in the presence of toluene. The results are shown in Table 3.

TABLE 3

| Exp | Catalyst | Cat amt (mmol) | Rxn mix | Ratio 1 (mmol) | Rxn vol (mL) | Ratio 2 | T (° C.) | time (h) | D inc. at $CH_2$ |
|---|---|---|---|---|---|---|---|---|---|
| 20 | Ru-MACHO-Cy | 0.0054 | | 2.21:15 | 0.5 | 400 | 110 | 16 | 0 |
| 21 | Ru-MACHO-Cy + NaBH4 (14 eq/Ru) | 0.0125 | | 5.45:34 | 1 | 450 | 80 | 16 | 0 |
| 22 | $RuCl_2(PPh_3)_3$ | | | 2.57:71 | | 150 | 150 | 30 min | 0 |
|  |  |  |  |  |  |  |  | 60 min | 0 |
| 23 | $Ru(PPh_3)_3Cl_2$ + $NaBH_4$ (18 eq/Ru) | 0.0091 | | 5.45:34 | 1 | 600 | 80 | 16 | 0 |
| 24 | $Ru(PPh_3)_3Cl_2$ | 0.0108 | | 5.45:34 | 1 | 500 | 80 | 16 | 0 |
| 25 | $Ru(PPh_3)_3Cl_2$ + AgOTf (5 eq/Ru) | 0.0094 | | 5.45:34 | 1 | 600 | 80 | 16 | 0 |
| 26 | $Ru(Acac)_3$ + TriPhos | | | 1.7:118 | | 104 | 150 | 10 min | 0 |
| 27 | $Ru(H)(BH_4)(dppp)(dpen)$ | 0.0109 | | 4.42:30 | 1 | 400 | 80 | 16 | 0 |
| 28 | $Ru(H)(BH_4)(dppp)(dpen)$ | 0.0100 | Tol (1 mL) | 4.42:30 | 2 | 450 | 80 | 16 | 0 |
| 29 | Cp*Ir(BiPy)(OTf)2 | 0.0103 | | 5.45:34 | 1 | 550 | 80 | 16 | 0 |
| 30 | Cp*Ir(BiPy)(OTf)2 | 0.0100 | Tol (1 mL) | 5.45:34 | 2 | 550 | 80 | 16 | 0 |
| 31 | $[Cp*IrCl_2]_2$ | 0.0095 | | 5.45:34 | 1 | 600 | 80 | 16 | 0 |
| 32 | $[Cp*IrCl_2]_2$ + $NaBH_4$ (19 eq/Ir) | 0.0080 | | 5.45:34 | 1 | 700 | 80 | 16 | 0 |
| 33 | $[Cp*IrCl_2]_2$ + AgOTf (3 eq/Ru) | 0.0099 | | 5.45:34 | 1 | 550 | 80 | 16 | 0 |
| 34 | $NaBH_4$ | 0.1900 | | 5.45:34 | 1 | 30 | 80 | 16 | 12 |

Rxn Mix (Reaction mixture): all reaction mixtures contained $EtOH:D_2O$ and the shown co-solvent.
Ratio 1 = ratio of $EtOH:D_2O$.
Ratio 2 = mmolar ratio of EtOH:catalyst.

Experiments 20-27, 29, and 31-34:

When no co-solvent was used, no or almost no D incorporation occurred at the desired $CH_2$ position independent of the type of the catalyst.

Experiments 28 and 30:

When the catalyst was $Ru(H)(BH_4)(dppp)(dpen)$ or Cp*Ir(BiPy)(OTf)$_2$, no D incorporation occurred at the desired $CH_2$ position even in the presence of a co-solvent.

Experiment Set 4

Various types of catalysts were tested in the presence of a non-deuterated toluene and THF. The results are shown in Table 4.

TABLE 4

| Exp | Catalyst | Cat amt (mmol) | Rxn Mix | Ratio 2 | D inc. at $CH_2$ |
|---|---|---|---|---|---|
| 35 | Ru-MACHO ®-BH | 0.0107 | Tol | 400 | 89 |
| 36 | Ru-MACHO ®-BH | 0.0121 | THF | 350 | 83 |
| 37 | Ru-MACHO-Cy + 20 eq $NaBH_4$ | 0.0114 | Tol | 350 | 52 |
| 38 | Ru-MACHO-Cy + 15 eq $NaBH_4$ | 0.0125 | THF | 350 | 19 |
| 39 | Ru-Firmenich + 25 eq $NaBH_4$ | 0.0116 | Tol | 350 | 8 |
| 40 | Ru-Firmenich + 20 eq $NaBH_4$ | 0.0117 | THF | 350 | 12 |
| 41 | Ru-Noyori + 10 eq $NaBH_4$ | 0.0182 | Tol | 200 | 6 |
| 42 | Ru-Noyori + 15 eq $NaBH_4$ | 0.0137 | THF | 300 | 5 |
| 43 | $Ru(Cl)(H)(PPh_3)_3$•Tol | 0.0087 | Tol | 500 | 9 |
| 44 | $Ru(Cl)(H)(PPh_3)_3$•Tol | 0.0082 | THF | 500 | 14 |

Rxn Mix (Reaction mixture): all reaction mixtures contained $EtOH:D_2O$ and the shown co-solvent.
Ratio 2 = mmolar ratio of EtOH:catalyst.
$EtOH:D_2O$ ratio (mmol) 4.1:37.9
Reaction volume = 2 mL (1 mL $D_2O$:EtOH, 1 mL co-solvent)

Experiments 35-36:

The use of a non-deuterated co-solvent in combination with Ru-MACHO®-BH resulted in D incorporation at the desired $CH_2$ position.

Experiments 37-44:

The use of a co-solvent with other catalysts resulted in insufficient D incorporation at the desired $CH_2$ position.

Experiment Set 5

The influence of the molar ratio of $D_2O$:EtOH and the amount of the co-solvent on the degree of D incorporation was tested. In the following experiments, the molar ratio of $D_2O$ to EtOH was 46 compared to about 5-20 in Experiment set 1. The results are shown in Table 5.

TABLE 5

| Exp | Catalyst | Cat amt (mmol) | Rxn Mix | Tol (vol) | Ratio 2 | D inc. at $CH_2$ |
|---|---|---|---|---|---|---|
| 45 | Ru-MACHO ® -BH | 0.0107 | Tol | 1 | 95 | 97 |
| 46 | Ru-MACHO ® -BH | 0.0121 | Tol | 0.5 | 84 | 97 |

TABLE 5-continued

| Exp | Catalyst | Cat amt (mmol) | Rxn Mix | Tol (vol) | Ratio 2 | D inc. at $CH_2$ |
|---|---|---|---|---|---|---|
| 47 | Ru-MACHO®-BH | 0.0114 | Tol | 0.25 | 89 | 97 |
| 48 | Ru-MACHO®-BH | 0.0125 | Tol | 0.125 | 82 | 97 |

Rxn Mix (Reaction mixture): all reaction mixtures contained EtOH:$D_2O$ and the shown co-solvent.
Ratio 2 = mmolar ratio of EtOH:catalyst.
EtOH:$D_2O$ ratio (mmol) = 1:46
Reaction volume = 1 mL $D_2O$:EtOH + various volume of Tol The high molar ratio of $D_2O$:EtOH led to a very high D incorporation of 97%. The same level of D incorporation was obtained for all experiments, even when only 12% vol/vol of Toluene was used. This can be advantageous for increasing the loading of a reactor and therefore the productivity.

Numerous modifications and variations of the present invention are possible in light of the above teachings. It is therefore to be understood that within the scope of the appended claims, the invention may be practiced otherwise that as specifically described herein.

What is claimed is:

1. A process for the preparation of a deuterated ethanol of the formula (I)

$$CR^1R^2R^3CR^4R^5OD \quad (I)$$

comprising: reacting ethanol with $D_2O$ in the presence of a ruthenium catalyst of formula (III) or (IV) and a co-solvent, provided that when the catalyst is of formula (III), the reaction is performed in the presence of an alkali metal borohydride:

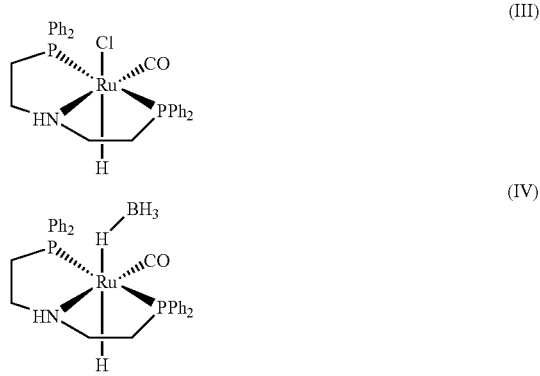

whererin:
R$^1$-R$^5$ are independently H or D, provided that the abundance of D in R$^4$ and R$^5$ is at least 80% and the abundance of D in R$^1$-R$^3$ is at most 25%; and,
the co-solvent is selected from tetrahydrofuran, toluene, 1,4-dioxane, diglyme and cyclopentyl methyl ether.

2. The process of claim 1, wherein the abundance of D in R$^4$ and R$^5$ is at least 90%.

3. The process of claim 1, wherein the abundance of D in R$^4$ and R$^5$ is at least 90% and the abundance of D in R$^1$-R$^3$ is at most 10%.

4. The process of claim 1, wherein the catalyst is of formula (III).

5. The process of claim 1, wherein the alkali metal borohydride is $NaBH_4$.

6. The process of claim 1, wherein the catalyst is of formula (III) and the reaction is performed in the absence of NaOH.

7. The process of claim 6, wherein the alkali metal borohydride is $NaBH_4$.

8. The process of claim 1, wherein the catalyst is of formula (IV).

9. The process of claim 1, wherein the catalyst is of formula (IV) and the reaction is performed in the absence of a base.

10. The process of claim 1, wherein the reacting step comprises,
a) reacting a first portion of $D_2O$ with ethanol to form a reacted mixture;
b) distilling the reacted mixture and collecting a distillate therefrom; and,
c) adding a second portion of $D_2O$ to the distillate to further react unreacted ethanol with $D_2O$.

11. The process of claim 10, wherein the molar ratio of $D_2O$ to ethanol mixed in each of the reaction sub-steps a) and c) is independently from 1-5.

12. The process of claim 1, wherein the reacting step comprises,
a) reacting a first portion of $D_2O$ with ethanol to form a first reacted mixture;
b) distilling the first reacted mixture and collecting a first distillate therefrom;
c) adding a second portion of $D_2O$ to the first distillate to further react with unreacted ethanol to form a second reacted mixture;
d) distilling the second reacted mixture and collecting a second distillate therefrom; and,
e) adding a third portion of $D_2O$ to the second distillate to further react with unreacted ethanol.

13. The process of claim 12, wherein the molar ratio of $D_2O$ to ethanol mixed in each of the reaction sub-steps a), c), and e) is independently from 1-5.

14. The process of claim 1, wherein the abundance of D in R$^4$ and R$^5$ is at least 95% and the abundance of D in R$^1$-R$^3$ is at most 5%.

15. The process of claim 1, wherein the abundance of D in R$^4$ and R$^5$ is at least 99.5% and the abundance of D in R$^1$-R$^3$ is at most 1%.

16. The process of claim 1, wherein the catalyst is of formula (IV) and the co-solvent is tetrahydrofuran.

17. The process of claim 1, wherein the catalyst is of formula (IV) and the co-solvent is toluene.

18. The process of claim 1, wherein the catalyst is of formula (IV) and the co-solvent is 1,4-dioxane.

19. The process of claim 1, wherein the catalyst is of formula (IV) and the co-solvent is diglyme.

20. The process of claim 1, wherein the catalyst is of formula (IV) and the co-solvent is cyclopentyl methyl ether.

21. The process of claim 1, wherein the catalyst is of formula (III), the base is $NaBH_4$ and the co-solvent is toluene.

22. The process of claim 1, wherein the catalyst is of formula (III), the base is $NaBH_4$ and the co-solvent is 1,4-dioxane.

23. The process of claim 1, wherein the catalyst is of formula (III), the base is $NaBH_4$ and the co-solvent is diglyme.

24. The process of claim 1, wherein the catalyst is of formula (III), the base is $NaBH_4$ and the co-solvent is cyclopentyl methyl ether.

* * * * *